(12) United States Patent
Shim et al.

(10) Patent No.: US 10,865,386 B2
(45) Date of Patent: Dec. 15, 2020

(54) ADULT STEM CELLS DERIVED FROM HUMAN SKIN DERMIS

(71) Applicant: AMOREPACIFIC CORPORATION, Seoul (KR)

(72) Inventors: Joong Hyun Shim, Yongin-si (KR); Seung Ha Yang, Yongin-si (KR); Tae Ryong Lee, Yongin-si (KR); Hak Hee Kang, Yongin-si (KR); Dong Wook Shin, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 101 days.

(21) Appl. No.: 15/402,060

(22) Filed: Jan. 9, 2017

(65) Prior Publication Data

US 2017/0114326 A1    Apr. 27, 2017

Related U.S. Application Data

(62) Division of application No. 14/240,330, filed as application No. PCT/KR2012/006780 on Aug. 24, 2012, now abandoned.

(30) Foreign Application Priority Data

Aug. 24, 2011    (KR) .................... 10-2011-0084768

(51) Int. Cl.
| | |
|---|---|
| *C12N 5/0775* | (2010.01) |
| *C12N 5/071* | (2010.01) |
| *A61K 35/35* | (2015.01) |
| *A61K 35/32* | (2015.01) |
| *A61K 35/28* | (2015.01) |
| *C12Q 1/6881* | (2018.01) |
| *G01N 33/74* | (2006.01) |
| *A61K 35/36* | (2015.01) |

(52) U.S. Cl.
CPC ............ *C12N 5/0668* (2013.01); *A61K 35/28* (2013.01); *A61K 35/32* (2013.01); *A61K 35/35* (2013.01); *C12N 5/0625* (2013.01); *C12Q 1/6881* (2013.01); *G01N 33/74* (2013.01); *A61K 35/36* (2013.01); *C12N 2533/54* (2013.01); *C12Q 2600/158* (2013.01); *G01N 2333/475* (2013.01); *G01N 2333/485* (2013.01); *G01N 2333/49* (2013.01); *G01N 2333/50* (2013.01)

(58) Field of Classification Search
None
See application file for complete search history.

(56) References Cited

U.S. PATENT DOCUMENTS

| | | | | |
|---|---|---|---|---|
| 5,436,135 | A | * 7/1995 | Tayot | ................. A61L 27/3604 435/68.1 |
| 2009/0274770 | A1 | 11/2009 | Gammelsaeter et al. | |
| 2010/0022003 | A1 | 1/2010 | Kang | |

FOREIGN PATENT DOCUMENTS

| | | | |
|---|---|---|---|
| JP | 2003531604 A | 10/2003 | |
| JP | 2010503727 | 2/2010 | |
| KR | 10-2006-0016540 | * 2/2006 | ............... C12N 5/06 |
| KR | 1020060016540 | 2/2006 | |
| KR | 1020100067277 | 6/2010 | |
| WO | 2011007900 A1 | 1/2011 | |
| WO | 2011034106 A1 | 3/2011 | |

OTHER PUBLICATIONS

Jones et al., Cell, vol. 80, pp. 83-93, 1995.*
Parish et al., Int. J. Cancer: vol. 52, pp. 378-383, 1992.*
Totonchi et al., Int. J. Dev. Biol. vol. 54: paes 877-886, 2010.*
Zhang et al., J. Cell. Mol. Med., vol. 14, No. 5, 2010, pp. 1135-1145.*
Bartsch et al., Stem Cells and Development 14:337-348, 2005.*
Salasznyk et al., Journal of Biomedicine and Biotechnology, 2004:1 (2004) pp. 24-34.*
Japanese Office Action—JP Application No. 2014-527079 dated Feb. 9, 2017, citing reference listed within.
Soma Tsutomuta et al., "Regenerative medicine", (2010), vol. 9, pp. 239.
Advanced Biomatrix, Collagen, Type IV, Human, (2009), p. 1; retrieved from the internet <URL:http://www.blossombio.com/pdf/products/UG_ABM_5022.pdf.
Angela Webb, et al., "Location and phenotype of human adult keratinocyte stem cells of the skin," Differentiation, 2004, vol. 72, p. 387-395.
Biernaskie et al., "SKPs Derive from Hair Follicle Precursors and Exhibit Properties of Adult Dermal Stem Cells", Cell Stem Cell, 5, Dec. 4, 2009, pp. 610-623.
Byrne et al., Enhanced Generation of Induced Pluripotent Stem Cells from a Subpopulation of Human Fibrolbasts, PlosONE, vol. 4, Issue 9, (2009), pp. 1-9.
Cellagen, Collagen Solutions for Tissue Culture, (2006), pp. 1-5; retrieved from the Internet <URL:http://www.mpbio.com/detailed_info.php?family_key=02152394.

(Continued)

*Primary Examiner* — Scott Long
*Assistant Examiner* — Evelyn Y Pyla
(74) *Attorney, Agent, or Firm* — Cantor Colburn LLP

(57) ABSTRACT

Provided in the present invention are adult stem cells derived from human skin dermis, and a method for isolating same. Further provided in the present invention are osteoblastic cells and adipocytes differentiated from the adult stem cells derived from human skin dermis, and a differentiation method therefor. Further provided in the present invention is a composition for osteogenesis or lipogenesis containing the stem cells, osteoblastic cells, or adipocytes. The isolation method of the present invention enables the adult stem cells derived from human skin dermis to be obtained in an easy and simple manner at a high yield rate. Genes and growth factors which are specifically expressed in the adult stem cells derived from human skin dermis isolated using the method can be separated, identified, and used later.

5 Claims, 7 Drawing Sheets

(56) References Cited

OTHER PUBLICATIONS

Chinese Office Action—CN Application No. 201280041267.4 dated Dec. 24, 2014, citing "Multilineage differentiation potential of human dermal skin-derived fibroblasts.".

Fu et al., Adiposcience, vol. 2, No. 3, 2005, pp. 306-311.

Fu Guo Chen, et al., "Clonal analysis of nestin—vimentin+ multipotent fibroblasts isolated from human dermis," Journal of Cell Science, 2007, vol. 120, No. 16, p. 2875-2883.

International Search Report—PCT/KR2012/006780 dated Nov. 16, 2012.

Japanese Office Action for Japanese Patent Application No. 2014-527079 dated Jul. 26, 2016 with a brief English Translation.

Jean G. Toma, et al., "Isolation and Characterization of Multipotent Skin-Derived Precursors from Human Skin," Stem Cells, 2005, vol. 23, p. 727-737.

Jean G. Toma, et al., "Isolation of multipotent adult stem cells from the dermis of mammalian skin," Nature Cell Biology, Sep. 2001, vol. 3, p. 778-784.

Kazutoshi Takahashi et al., "Induction of Pluripotent Stem Cells from Adult Human Fibroblasts by Defined Factors," Cell, vol. 131, Nov. 30, 2007,.

Korean Office Action—Korean Application No. 10-2011-0084768 dated Mar. 7, 2016, citing the reference listed within.

Lorenz et al., "Multilineage differentiation potential of human dermal skin-derived fibroblasts", Experimental Dermatology, vol. 17, Feb. 28, 2008, 925-932.

Luis A. Garza, "Bald scalp in men with androgenetic alopecia retains hair follicle stem cells but lacks CD200-rich and CD34-positive hair follicle progenitor cells," The Journal of Clinical Investigation, Feb. 2011, vol. 121, No. 2, p. 613-622.

Pehr Sommar, "Differentiation of Human Dermal Fibroblasts and Applications in Tissue Engineering", Linköping University Medical Dissertations, No. 1202, (2010), pp. 1-136.

Raymond L. Page et al., "Induction of Stem Celll Gene Expression in Adult Human Fibroblasts without Transgenes," Cloning and Stem Cells, vol. 11, No. 3, 2009, p. 417-426.

Rui Yi, et al., "A skin microRNA promotes differentiation by repressing 'stemness'," Nature, Mar. 13, 2008, vol. 452, p. 225-229.

Shim et al., Enrichment and characterization of human dermal stem/progenitor cells using collagen type IV, Letters to the Editor, Journal of Dermatological Science 67 (2012), pp. 202-205, published online Jun. 2012.

Takahashi et al., "Induction of Pluripotent Stem Cells from Adult Human Fibroblasts by Defined Factors", Cell, 131, Nov. 30, 2007. pp. 861-872.

Written Opinion—PCT/KR2012/006780 dated Nov. 16, 2012.

Yamamoto et al., "Progress in the culture method of bone cells", Nihon Rinsho, vol. 48(12), 1990, pp. 2742-2748.

\* cited by examiner

ADULT STEM CELLS DERIVED FROM HUMAN SKIN DERMIS

CROSS REFERENCE TO RELATED APPLICATIONS

This application is a divisional of U.S. application Ser. No. 14/240,330, filed on Feb. 21, 2014, which is a National Stage application of PCT/KR2012/006780, filed Aug. 24, 2012, which claims the benefit of Korean Patent Application No. 10-2011-0084768, filed on Aug. 24, 2011, each of which is incorporated by reference in their entirety herein.

TECHNICAL FIELD

The present disclosure relates to human skin dermis-derived adult stem cells.

BACKGROUND ART

In recent years, efforts have been consistently made to isolate adult stem cells having pluripotency from tissues. Although these adult stem cells are disadvantageous in that they cannot differentiate into all cell types unlike the totipotent embryonic stem cells, they are useful in researches and applications since they are free from the ethical issues of the embryonic stem cells. However, since the number of the adult stem cells is very small (predicted to be less than about 1-5% of the cells in the corresponding tissue) unlike the embryonic stem cells, there is a difficulty in harvesting and isolating them from adult tissues.

Ultimately, the main purpose of stem cell researches is for therapy. It is expected that the health of patients with diseases in specific organs or tissues can be recovered through cell transplantation or replacement of providing new stem cell-based cells. Human skin adult stem cells are studied with the expectation that they can be used to treat skin damage such as burn or wound or skin diseases such as ulcer, atopy, etc. The human skin consists of the epidermis, the dermis, the subcutis and appendages. Epidermal stem cells have been isolated from the epidermis and hair follicle stem cells have been isolated from the appendage hair. And, dermis-derived adult stem cells have been isolated from rodents and human through a special culture system called suspension culture. These dermis-derived adult stem cells (also known as skin derived precursors (SKPs)) have been found to be isolable as mesodermal cells such as fat, bone and muscle cells (Toma et al., 2001; Toma et al., 2005).

The skin adult stem cells account for a very small number in the skin tissue. It is estimated that the number of the epidermal stem cells account is smaller than 1-5% of the number of keratinocytes, and the number of the dermis-derived stem cells is also estimated to be only 2-3%. Accordingly, there is a difficulty in isolating them, but few specific markers (or biomarkers) for isolating the skin adult stem cells have been reported. At present, integrin alpha-6, CD71, integrin beta-1 and p63 are known as markers of the epidermal stem cells (Webb et al., 2004; Yi et al., 2008), and only CD200 is known for the hair follicle stem cells (Garza et al., 2011).

Recently, it was observed that dermis-derived adult stem cells isolated from the human dermis using a dermal fibroblast culture system have the pluripotency to differentiate into fat, bone and cartilage cells and they were found to be vimentin+/nestin− (Chen F G et al., 2007). However, the cells could not be isolated effectively because the method is not quite different from that of the ordinary fibroblast culture system.

DISCLOSURE

Technical Problem

The present disclosure is directed to providing human skin dermis-derived adult stem cells isolated from human skin, which express specific genes and growth factors as biomarkers.

Technical Solution

In a general aspect, the present disclosure provides human skin dermis-derived adult stem cells wherein one or more gene selected from a group consisting of Sox2(SRY (sex determining region Y)-box 2) and S100b(S100 calcium binding protein B] is overexpressed as compared to human skin dermis-derived fibroblasts.

In an exemplary embodiment of the present disclosure, the stem cells may be obtained by subculturing human skin dermis-derived fibroblasts, reacting the cells with gelatin or type 4 collagen and separating the cells adhering to the gelatin or type 4 collagen.

In an exemplary embodiment of the present disclosure, the stem cells may be obtained by reacting the fibroblasts with gelatin or type 4 collagen for 1-5 minutes.

In an exemplary embodiment of the present disclosure, the gelatin may be one dissolved in distilled water to a concentration of 0.1-1 wt % and the type 4 collagen may be one dissolved in distilled water to a concentration of 10-30 µg/mL.

In an exemplary embodiment of the present disclosure, the gelatin or the type 4 collagen may be one coated on a substrate at 0-10° C. for 16-24 hours.

In an exemplary embodiment of the present disclosure, the stem cells may be ones wherein one or more growth factor selected from a group consisting of EGF (epidermal growth factor), FGF4(fibroblast growth factor 4), PDGF-AA (platelet-derived growth factor-AA), VEGFR-2(vascular endothelial growth factor receptor 2), VEGFR-3(vascular endothelial growth factor receptor 3) and VEGF-D (vascular endothelial growth factor D) is overexpressed as compared to human skin dermis-derived fibroblasts.

In an exemplary embodiment of the present disclosure, the stem cells may be stem cells of Accession No: KCTC11995BP.

In another general aspect, the present disclosure provides osteoblasts or adipocytes differentiated from the human skin dermis-derived adult stem cells.

In an exemplary embodiment of the present disclosure, the osteoblasts may be ones wherein one or more gene selected from a group consisting of OGN (osteoglycin) and ACAN (aggrecan) is overexpressed as compared to skin dermis-derived fibroblasts.

In an exemplary embodiment of the present disclosure, the adipocytes may be ones wherein one or more gene selected from a group consisting of PPARG (peroxisome proliferator-activated receptor gamma), LEP (leptin), AdipoQ (adiponectin, C1Q and collagen domain containing) and FABP4(fatty acid binding protein 4, adipocyte) is overexpressed as compared to skin dermis-derived fibroblasts.

In another general aspect, the present disclosure provides a composition for osteogenesis or adipogenesis, containing the human skin dermis-derived adult stem cells, osteoblasts or adipocytes as an active ingredient.

In an exemplary embodiment of the present disclosure, the composition may provide the effect of preventing and treating osteoporosis, preventing and treating skin aging, treating skin wound, improving skin blood circulation, enhancing skin volume or skin grafting.

In another general aspect, the present disclosure provides a method for isolating human skin dermis-derived adult stem cells, including subculturing human skin dermis-derived fibroblasts, reacting the cells with gelatin or type 4 collagen and separating the cells adhering to the gelatin or type 4 collagen.

In an exemplary embodiment of the present disclosure, in the isolation method, the fibroblasts may be reacted with gelatin or type 4 collagen for 1-5 minutes.

In an exemplary embodiment of the present disclosure, in the isolation method, the gelatin may be dissolved in distilled water to a concentration of 0.1-1 wt % and the type 4 collagen may be dissolved in distilled water to a concentration of 10-30 μg/mL and then reacted with the fibroblasts.

In an exemplary embodiment of the present disclosure, in the isolation method, the gelatin or the type 4 collagen may be coated on a substrate at 0-10° C. for 16-24 hours and then reacted with the fibroblasts.

In an exemplary embodiment of the present disclosure, the isolation method may further include confirming whether one or more gene selected from a group consisting of Sox2(SRY (sex determining region Y)-box 2) and S100b (S100 calcium binding protein B) is overexpressed as compared to skin dermis-derived fibroblasts In an exemplary embodiment of the present disclosure, the isolation method may further include confirming whether one or more growth factor selected from a group consisting of EGF (epidermal growth factor), FGF4(fibroblast growth factor 4), PDGF-AA (platelet-derived growth factor-AA), VEGFR-2(vascular endothelial growth factor receptor 2), VEGFR-3(vascular endothelial growth factor receptor 3) and VEGF-D (vascular endothelial growth factor D) is overexpressed as compared to skin dermis-derived fibroblasts.

In another general aspect, the present disclosure provides a method for differentiating human skin dermis-derived adult stem cells, including differentiating the human skin dermis-derived adult stem cells isolated by the isolation method into osteoblasts or adipocytes.

In an exemplary embodiment of the present disclosure, the differentiation method may include: differentiating the isolated stem cells in an osteogenic differentiation medium; and confirming whether the differentiated cells overexpress one or more gene selected from a group consisting of OGN (osteoglycin) and ACAN (aggrecan) as compared to skin dermis-derived fibroblasts.

In an exemplary embodiment of the present disclosure, the differentiation method may include: differentiating the isolated stem cells in an adipogenic differentiation medium; and confirming whether the differentiated cells overexpress one or more gene selected from a group consisting of PPARG (peroxisome proliferator-activated receptor gamma), LEP (leptin), AdipoQ (adiponectin, C1Q and collagen domain containing) and FABP4(fatty acid binding protein 4, adipocyte) as compared to skin dermis-derived fibroblasts.

Advantageous Effects

A composition containing the human skin dermis-derived adult stem cells of the present disclosure, osteoblasts differentiated from the stem cells or adipocytes differentiated from the stem cells may be used as a composition for osteogenesis or adipogenesis. Further, an isolation method according to the present disclosure allows easy and simple acquisition of skin dermis-derived adult stem cells in high yield and also allows utilization of genes and growth factors specifically expressed in the isolated skin dermis-derived adult stem cells.

BEST MODE

Figure 1:
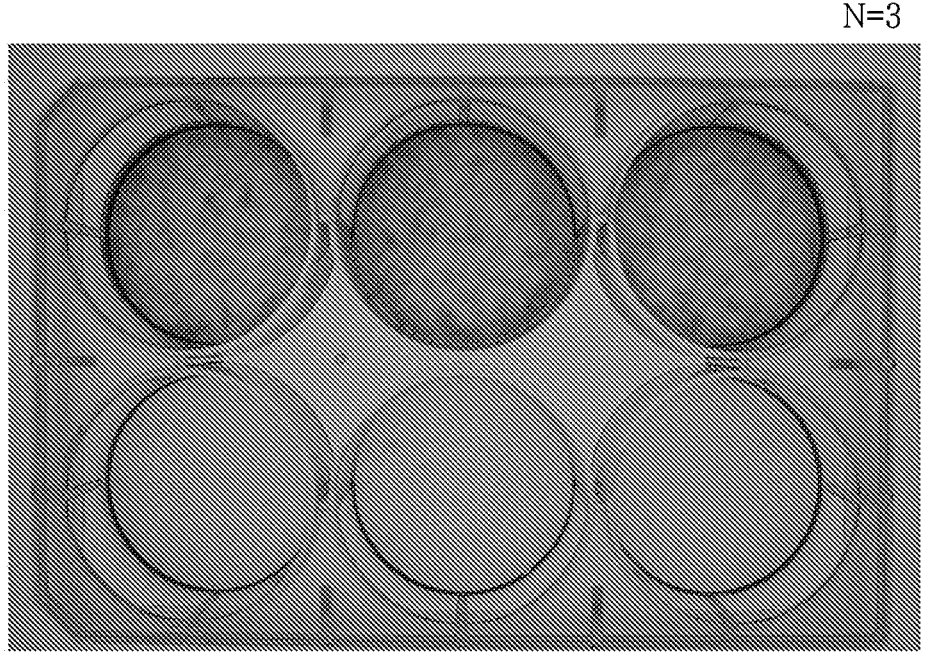
FIG. 1 shows a result of comparing the colony forming ability of skin dermis-derived adult stem cells and skin dermis-derived fibroblasts separated using gelatin as a measure of sternness.

Hereinafter, the present disclosure is described in detail.

The inventors of the present disclosure have made efforts to develop a method for isolating human dermis-derived adult stem cells, which have not been fully elucidated when compared with epidermal stem cells or hair follicle stem cells, in high yield. In doing so, they have found that the adhesion of the cells to gelatin or type 4 collagen changes with time and have completed the present disclosure based on the finding.

The present disclosure provides human skin dermis-derived adult stem cells wherein one or more gene selected from a group consisting of Sox2(SRY (sex determining region Y)-box 2) and S100b (S100 calcium binding protein B) is overexpressed as compared to human skin dermis-derived fibroblasts.

The Sox2(SRY (sex determining region Y)-box 2) and the S100b (S100 calcium binding protein B) show specifically increased expression in the skin dermis-derived adult stem cells of the present disclosure among various kinds of genetic markers of human adult stem cells and it has been first identified by the inventors of the present disclosure.

The previous known skin dermis-derived adult stem cells are known to be nestin-(nonexpression), vimentin+(expression). Since the skin dermis-derived adult stem cells isolated in the present disclosure show no difference in the expression of nestin and vimentin as compared to the skin dermis-derived fibroblasts, they are different from the existing skin dermis-derived adult stem cells.

Isolation of skin adult stem cells using type 4 collagen is known only for the epidermal stem cells among the various kinds of skin adult stem cells. The skin dermis-derived adult stem cells of the present disclosure are novel stem cells which are different from the existing skin dermis-derived adult stem cells and were first invented by the inventors of the present disclosure.

The present disclosure also provides a method for isolating skin dermis-derived adult stem cells, including subculturing human skin dermis-derived fibroblasts for 2 or 3 passages, reacting the cells with gelatin or type 4 collagen and separating the cells adhering to the gelatin or type 4 collagen, and human skin dermis-derived adult stem cells isolated by the isolation method.

The reaction may be conducted for 1-5 minutes, specifically 4-5 minutes. If the reaction time is shorter than 1 minute, the stem cells may not be obtained in good yield. And, if the reaction time is longer than 5 minutes, other fibroblasts may be mixed into the stem cells. That is to say, if the reaction time is about 5-30 minutes, about 50-60% of the cells adhering to the type 4 collagen or gelatin are other fibroblasts adhering due to gravity.

The concentration of the gelatin or the type 4 collagen may be 0.1-1% (weight/solvent volume, for gelatin) or 10-30 μg/mL (for type 4 collagen). The solvent may be distilled water, specifically triply distilled water. The collagen may be prepared into a 1 mg/mL stock solution in 0.25% acetic acid and then diluted with triply distilled water for use.

Further, the gelatin or type 4 collagen may be one coated on a substrate at 0-10° C., specifically 4° C., for 16-24 hours.

The substrate may be selected from a group consisting of polyethylene, polypropylene, polyethylene-polypropylene copolymer, metal, silicon and glass, but is not limited thereto. The metal may be nickel, gold or silver, but is not limited thereto. Specifically, the substrate may be a commonly used culture vessel. The substrate is not particularly limited in shape. For example, the substrate may be in the form of spherical particles, plate, tube, and so forth. The coating may be conducted according to a known method.

The isolation method may further include confirming whether the isolated cells overexpress one or more gene selected from a group consisting of Sox2(SRY (sex determining region Y)-box 2) and S100b (S100 calcium binding protein B) as compared to human skin dermis-derived fibroblasts.

The isolation method may further include confirming whether the isolated cells overexpress one or more growth factor selected from a group consisting of EGF (epidermal growth factor), FGF4(fibroblast growth factor 4), PDGF-AA (platelet-derived growth factor-AA), VEGFR-2(vascular endothelial growth factor receptor 2), VEGFR-3(vascular endothelial growth factor receptor 3) and VEGF-D (vascular endothelial growth factor D) as compared to human skin dermis-derived fibroblasts. The skin dermis-derived adult stem cells isolated in the present disclosure may overexpress one or more growth factor selected from a group consisting of EGF (epidermal growth factor), FGF4(fibroblast growth factor 4), PDGF-AA (platelet-derived growth factor-AA), VEGFR-2(vascular endothelial growth factor receptor 2), VEGFR-3(vascular endothelial growth factor receptor 3) and VEGF-D (vascular endothelial growth factor D) as compared to skin dermis-derived fibroblasts.

The present disclosure also provides a method for differentiating human skin dermis-derived adult stem cells, including differentiating the human skin dermis-derived adult stem cells isolated by the isolation method into osteoblasts or adipocytes, and osteoblasts or adipocytes differentiated from the human skin dermis-derived adult stem cells.

In the differentiation method, the isolated stem cells may be differentiated in an osteogenic differentiation medium (hMSC mesenchymal stem cell osteogenic differentiation medium, Lonza PT-3002) for 14 days, while replacing the medium once in 2-3 days (see Example 4). The differentiation method may further include confirming whether the differentiated cells overexpress one or more gene selected from a group consisting of OGN (osteoglycin) and ACAN (aggrecan) as compared to skin dermis-derived fibroblasts. The osteoblasts differentiated in the present disclosure may overexpress one or more gene selected from a group consisting of OGN (osteoglycin) and ACAN (aggrecan) as compared to skin dermis-derived fibroblasts.

In the differentiation method, the isolated stem cells may be differentiated in an adipogenic differentiation medium, specifically DMEM medium, more specifically DMEM medium containing 10% fetal bovine serum, 0.1% insulin, 1 μM dexamethasone, 0.5 mM IBMX and 1 μM troglitazone, for 7 days, while replacing the medium at 2-3 day intervals (see Example 5). The differentiation method may further include confirming whether the differentiated cells overexpress one or more gene selected from a group consisting of PPARG (peroxisome proliferator-activated receptor gamma), LEP (leptin), AdipoQ (adiponectin, C1Q and collagen domain containing) and FABP4(fatty acid binding protein 4, adipocyte) as compared to skin dermis-derived fibroblasts. The adipocytes differentiated in the present disclosure may overexpress one or more gene selected from a group consisting of PPARG, LEP, AdipoQ and FABP4 as compared to human skin dermis-derived fibroblasts.

The present disclosure also provides a composition for osteogenesis or adipogenesis, containing the skin dermis-derived adult stem cells, the osteoblasts differentiated from the skin dermis-derived adult stem cells or the adipocytes differentiated from the skin dermis-derived adult stem cells as an active ingredient. The composition according to the present disclosure composition provides the effect of preventing and treating osteoporosis, preventing and treating skin aging, treating skin wound, improving skin blood circulation, enhancing skin volume or skin grafting. The composition may be in any form commonly applied to skin. Specifically, it may be a composition for external application on skin, such as a cosmetic composition or a pharmaceutical composition.

The cosmetic composition may be, for example, a basic cosmetic composition, a makeup cosmetic composition, a hair cosmetic composition, a body cosmetic composition, etc., and is not particularly limited in formulation type.

For example, the cosmetic composition may be formulated into solution, suspension, emulsion, paste, gel, cream, lotion, powder, soap, surfactant-containing cleanser, oil, powder foundation, emulsion foundation, wax foundation, spray, etc., but is not limited thereto. More specifically, it may be formulated into a basic cosmetic such as softening lotion, nourishing lotion, milk lotion, body lotion, nourishing cream, massage cream, moisturizing cream, hand cream, essence, eye cream, cleansing cream, cleansing foam, cleansing water, pack, gel, patch, oil-in-water (O/W) emulsion, water-in-oil (O/W) emulsion, etc., a coloring cosmetic such as lipstick, makeup base, foundation, etc., a cleanser such as shampoo, rinse, body cleanser, toothpaste, mouthwash, etc., or a hair care cosmetic such as hair tonic, hair fixative, e.g. gel or mousse, hairdye, etc.

The cosmetic composition may contain a cosmetically acceptable medium or matrix and may be provided as any topically applicable formulation, e.g., solution, gel, anhydrous solid or paste, oil-in-water emulsion, suspension, microemulsion, microcapsule, microgranule, ionic (liposome) and/or nonionic vesicular dispersion, cream, skin lotion, milk lotion, powder, ointment, spray or conceal stick. These compositions may be prepared according to a method commonly employed in the art.

When the formulation of the present disclosure is solution or emulsion, a solvent, a dissolving agent or an emulsifier may be used as a carrier. For example, water, ethanol, isopropanol, ethyl carbonate, ethyl acetate, benzyl alcohol, benzyl benzoate, propylene glycol, 1,3-butylene glycol, glycerol aliphatic ester, polyethylene glycol or fatty add ester of sorbitan may be used.

When the formulation of the present disclosure is suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier.

When the formulation of the present disclosure is paste, cream or gel, animal oil, vegetable oil, wax, paraffin, starch, tragacanth, cellulose derivatives, polyethylene glycol, silicone, bentonite, silica, talc, zinc oxide, etc. may be used as a carrier.

When the formulation of the present disclosure is powder or spray, lactose, talc, silica, aluminum hydroxide, calcium silicate or polyamide powder may be used as a carrier. In particular, when the formulation is spray, it may further contain a propellent such as chlorofluorohydrocarbon, propane/butane or dimethyl ether.

When the formulation of the present disclosure is surfactant-containing cleanser, aliphatic alcohol sulfate, aliphatic alcohol ether sulfate, sulphosuccinic acid monoester, isethionate, imidazolinium derivatives, methyltaurate, sarcosinate, fatty acid amide ether sulfate, alkylamidobetain, aliphatic alcohol, fatty acid glyceride, fatty acid diethanolamide, vegetable oil, lanolin derivatives, ethoxylated glycerol fatty acid ester, etc. may be used as a carrier.

In an exemplary embodiment of the present disclosure, the cosmetic composition of the present disclosure may further contain a thickener. The thickener contained in the cosmetic composition of the present disclosure may be methyl cellulose, carboxymethyl cellulose, carboxymethyl hydroxyguanine, hydroxymethyl cellulose, hydroxyethyl cellulose, carboxyvinyl polymer, polyquaternium, cetearyl alcohol, stearic acid, carrageenan, etc. Specifically, one or more selected from a group consisting of carboxymethyl cellulose, carboxyvinyl polymer and polyquatemium may be used. Most specifically, carboxyvinyl polymer may be used.

In an exemplary embodiment of the present disclosure, the cosmetic composition may contain various adequate matrices and additives as desired and their kind and amount can be easily determined by those skilled in the art. The cosmetic composition may contain acceptable additives commonly used in the art, such as preservative, colorant, etc.

Specifically, the preservative may be phenoxyethanol, 1,2-hexanediol, etc. and a synthetic fragrance may be used.

Further, the cosmetic composition of the present disclosure may contain a substance selected from a group consisting of water-soluble vitamin, oil-soluble vitamin, polypeptide, polysaccharide, sphingolipid and seaweed extract. In addition, it may further contain oil, fat, humectant, emollient, surfactant, organic or inorganic pigment, organic powder, UV absorbent, preservative, sterilizer, antioxidant, plant extract, pH control agent, alcohol, colorant, fragrance, blood circulation stimulant, cooling agent, antiperspirant, purified water, etc.

However, the ingredients that may be contained in the cosmetic composition are not limited thereto. And, the amount of the ingredients may be determined within the range not negatively affecting the purpose and effect of the present disclosure.

In an exemplary embodiment of the present disclosure, the pharmaceutical composition may be prepared into a solid, semi-solid or liquid formulation for parenteral administration by adding a commonly used inorganic or organic carrier, excipient or diluent to the skin dermis-derived adult stem cells as an active ingredient. The formulation for parenteral administration may be a formulation for transdermal administration selected from a group consisting of drip, ointment, lotion, gel, cream, patch, spray, suspension and emulsion, but is not limited thereto.

The carrier, excipient or diluent that may be contained in the composition may include lactose, dextrose, sucrose, oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate and mineral oil.

Each formulation of the composition may further contain the above-described ingredients selected by those skilled in the art considering the formulation type, purpose of use, etc. without difficulty. In this case, the additional ingredients may provide a synergic effect.

Further, when the composition according to the present disclosure is used as a pharmaceutical composition, it may further contain pharmaceutical adjuvants such as preservative, stabilizer, wetting or emulsifying accelerator, salt or buffer for control of osmotic pressure, etc. or other therapeutically useful substances and may be prepared into various formulations for oral or parenteral administration according to commonly employed methods.

The actual administration dosage of the active ingredient will be determined considering related factors such as severity of condition, selected administration route, age, sex, body weight and physical condition of a subject, or the like. A general administration dosage of the active ingredient is about 0.001-2000 mg/kg/day, more specifically 0.5-2.5 mg/kg/day. External application on skin may be performed once or several times a day.

MODE FOR INVENTION

Hereinafter, the present disclosure will be described in detail through examples. However, the following examples are for illustrative purposes only and it will be apparent to those of ordinary skill in the art that the scope of the present disclosure is not limited by the examples.

[Example 1] Isolation of RA/SA Cells from Human Dermis-Derived Fibroblasts Using Gelatin or Type 4 Collagen Human dermis-derived fibroblasts (normal human dermal fibroblasts, NHDF) were purchased from Lonza, Inc (Walkersville, Md., USA, NHDF-Ad-Der Fibroblasts, CC-2511). The human dermis-derived fibroblasts were subcultured on a 75-cm$^2$ T-flask under the condition of 37° C. and 5% $CO_2$ in a $CO_2$ incubator. The subculturing was conducted for 2 or 3 passages.

5 mL of 0.1-1% gelatin or 10-30 µg/mL type 4 collagen was coated on a 100-mm culture dish at 4° C. for 16-24 hours. After detaching the human dermis-derived fibroblasts from a 100-mm culture dish using 0.25% trypsin (trypsin-EDTA), the cells were centrifuged at 1200 rpm for 5 minutes. After removing culture medium, the cells were added to 5 mL of DMEM medium and then suspended. Then, the cells were incubated on the culture dish on which the gelatin or type 4 collagen had been coated for 5 minutes and were isolated as the cells adhering to the culture dish (RA; rapidly adhering) and those not adhering to the culture dish for in 5 minutes but adhering within 4 hours (SA; slowly adhering).

[Example 2] Colony Forming Assay of Isolated RA/SA Cells

Colony forming assay was conducted to compare the colony forming ability (stemness) of the RA/SA cells isolated using gelatin or type 4 collagen. The isolated RA/SA cells were seeded onto a 6-well culture dish, with 1×10$^2$ cells per well. After culturing for 14 days, the cells were stained with a solution containing 10% ethanol and 0.1% crystal violet for 5 minutes at room temperature, washed 4 times with phosphate buffered saline (PBS) and observed under a microscope.

The result is shown in FIG. 1. As can be seen from FIG. 1, the isolated RA cells showed increased colony forming ability (hereinafter, the RA cells are referred to as human dermis-derived adult stem cells and the SA cells are referred to as human dermis-derived fibroblasts). The inventors of the present disclosure have deposited the human dermis-derived adult stem cells isolated in the present disclosure with the Korean Collection for Type Cultures (KCTC) of Korea Research Institute of Bioscience and Biotechnology (KRIBB) under the accession number KCTC11995BP on Aug. 8, 2011.

[Example 3] Selection of Genetic Markers of Human Dermis-Derived Adult Stem Cells Through Measurement of mRNA Expression The human dermis-derived adult stem cells isolated in Example 1 and dermis-derived fibroblasts were washed with 2 mL of PBS and RNA was isolated from the cells using TRIZOL® reagent (Invitrogen, Carlsbad, Calif., USA). The isolated RNA was purified once again using the Qiagen RNEASY® kit (Qiagen, Valencia, Calif.) and the quality of the RNA was analyzed using the Agilent 2100 Bioanalyzer (Agilent Technologies, Santa Clara, Calif., USA). cDNA was synthesized from the RNA using the SUPERSCRIPT® Reverse Transcriptase (RT) kit (Invitrogen, Carlsbad, Calif.) and quantitatively analyzed by real-time reverse transcription polymerase chain reaction (Q-RT-PCR).

Figure 2:
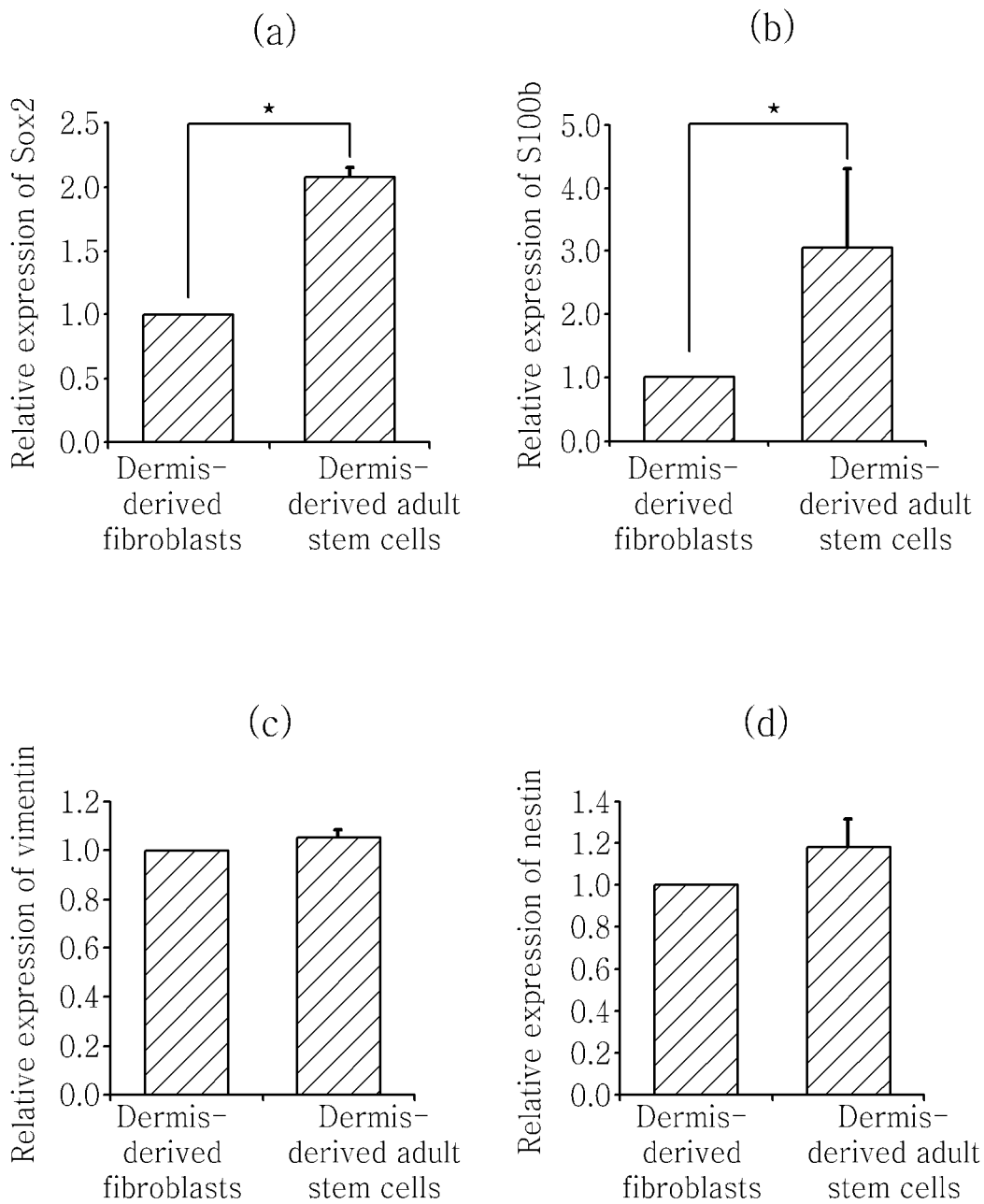
FIG. 2 shows that the expression of Sox2 (a) and S100b (b) is increased 2 and 3 times respectively in isolated skin dermis-derived adult stem cells as compared to dermis-derived fibroblasts. It was investigated whether the stem cells are identical or similar to the human dermis-derived adult stem cells isolated by the existing method (vimentin+/nestin−). Both vimentin (c) and nestin (d) were expressed as in the dermis-derived fibroblasts, suggesting that the human dermis-derived adult stem cells of the present disclosure are different from the human dermis-derived adult stem cells isolated by the existing method (vimentin+/nestin−) (Chen F G et al., 2007).

The change in the expression pattern of Sox2 and S100b genes, which are known as characteristic genetic markers of the adult stem cells, in the isolated human dermis-derived adult stem cells and the dermis-derived fibroblasts was analyzed using the TAQMAN® gene expression assay kit (Applied Biosystems, Foster City, Calif.) (Sox2 gene primer: Hs01053049_s1, S100b gene primer: Hs00389217_m1). The result is shown in a and b of FIG. 2.

The isolated human dermis-derived adult stem cells showed about 2-3 times higher expression of the genes as compared to the human dermis-derived fibroblasts. Also, the expression of nestin (Hs00707120_s1) and vimentin (Hs00185584_m1) genes was investigated for comparison with the previously known human dermis-derived adult stem cells exhibiting nestin-/vimentin+. Both nestin (Hs00707120_s1) and vimentin (Hs00185584_m1) were expressed in the human dermis-derived adult stem cells isolated according to the present disclosure and no difference was found in the expression level as compared to the dermis-derived fibroblasts (c and d of FIG. 2). Accordingly, it can be seen that the human dermis-derived adult stem cells isolated according to the present disclosure are novel dermis-derived adult stem cells that have not been identified previously.

The increase in expression was statistically significant when tested by the paired Student's t-test with $p \leq 0.05$.

[Example 4] Confirmation of Differentiation Ability of Human Dermis-Derived Adult Stem Cells In order to confirm the differentiation ability of the human dermis-derived adult stem cells isolated with gelatin or type 4 collagen, the cells were induced to differentiate into osteoblasts and adipocytes.

Differentiation into osteoblasts was induced using an osteogenic differentiation medium (hMSC mesenchymal stem cell osteogenic differentiation medium, PT-3002) of Lonza, Inc. (Walkersville, Md., USA). The isolated human dermis-derived adult stem cells and dermis-derived fibroblasts were seeded onto a 6-well culture dish, with 20×10$^4$ cells per well, and differentiation was induced using the osteogenic differentiation medium for 14 days, which was confirmed through gene expression assay.

Differentiation into adipocytes was induced using DMEM medium containing 10% fetal bovine serum, 0.1% insulin, 1 µM dexamethasone, 0.5 mM IBMX and 1 µM troglitazone. The isolated human dermis-derived adult stem cells and dermis-derived fibroblasts were seeded onto a 6-well culture dish, with 20×10$^4$ cells per well, and differentiation was induced using the adipogenic differentiation medium for 7 days, which was confirmed through gene expression assay.

Figure 3:
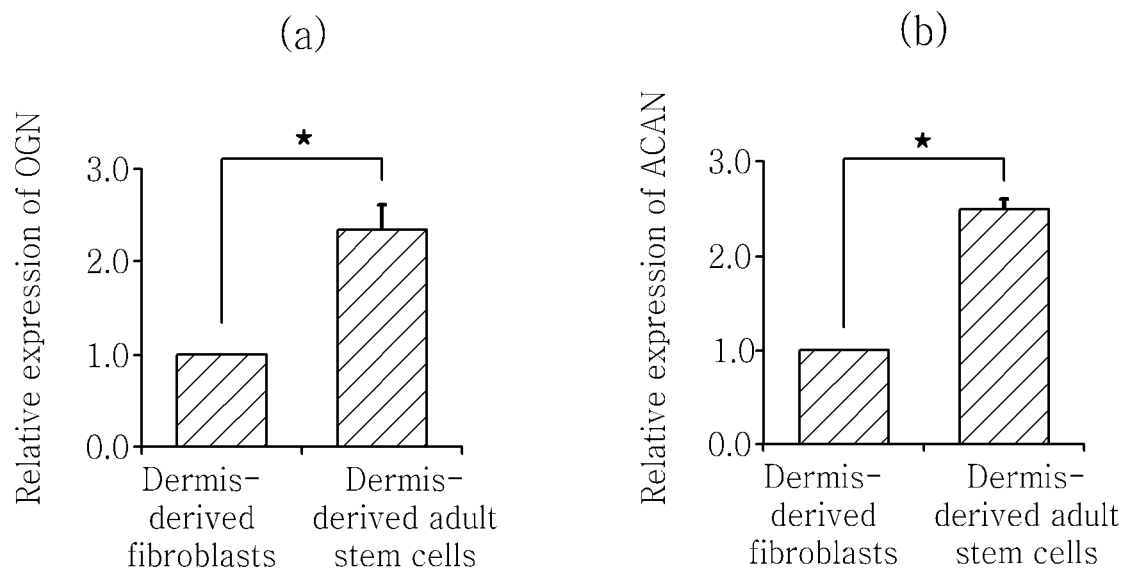
FIG. 3 shows that isolated skin dermis-derived adult stem cells differentiate into osteoblasts and representative genetic markers of osteoblasts, OGN (a) and ACAN (b), are expressed.
Figure 4:
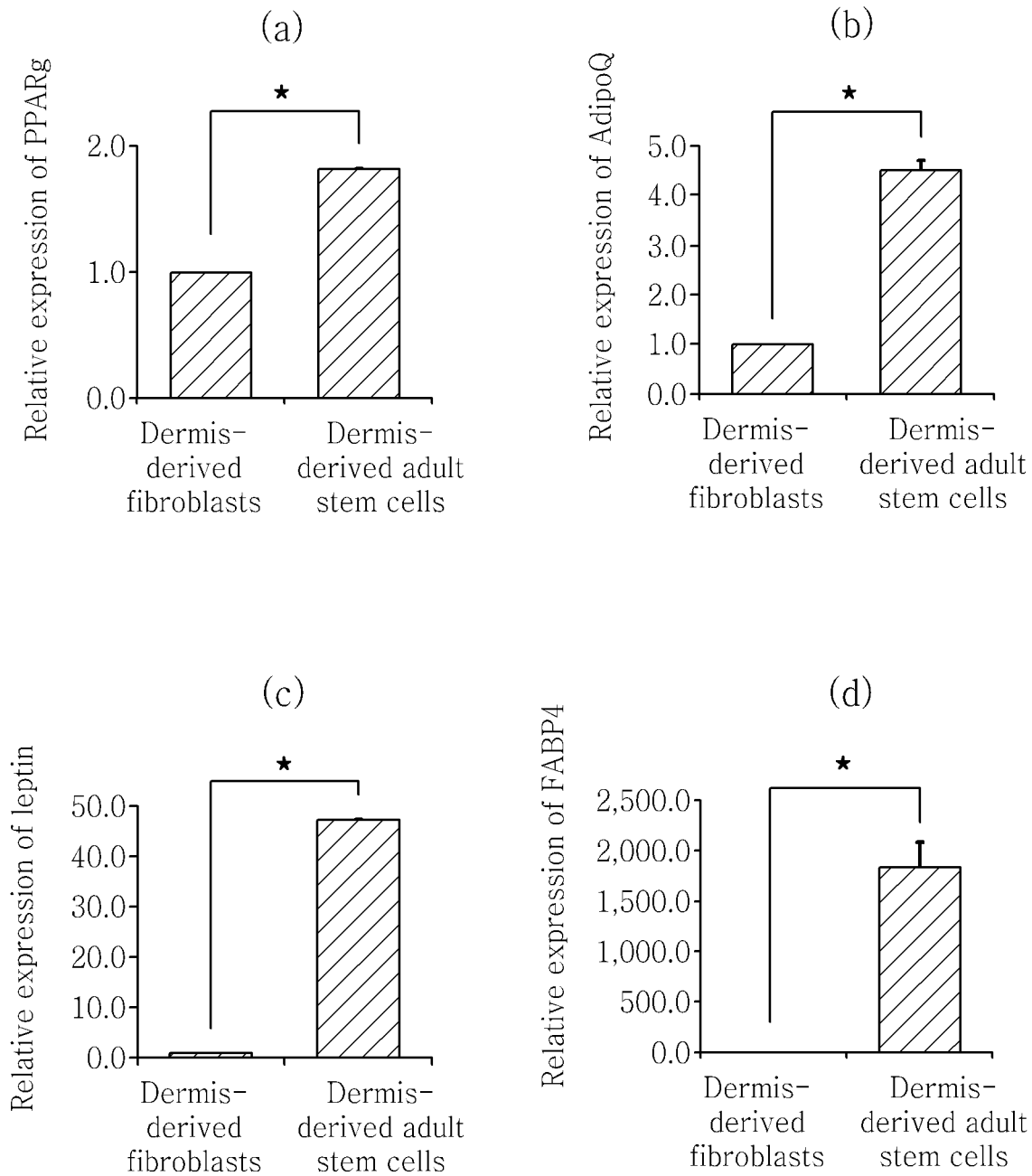
FIG. 4 shows that isolated skin dermis-derived adult stem cells differentiate into adipocytes and representative genetic markers of adipocytes, PPARG (a), AdipoQ (b), leptin (c) and FABP4 (d), are expressed.

[Example 5] Measurement of Expression of Differentiation Biomarkers in Osteoblasts and Adipocytes Differentiated from Isolated Human Dermis-Derived Adult Stem Cells and Dermis-Derived Fibroblasts After the isolated human dermis-derived adult stem cells and the dermis-derived fibroblasts were induced to differentiate into osteoblasts and adipocytes, respectively, the change in the expression pattern of OGN and ACAN, which are biomarkers of osteoblasts, and PPARG, leptin, AdipoQ and FABP4, which are biomarkers of adipocytes, was evaluated in the same manner as in Example 3 using the TAQMAN® gene expression assay kit (Applied Biosystems, Foster City, Calif.) (OGN gene primer: Hs00247901_m1, ACAN gene primer: Hs00153936_m1, PPARG gene primer: Hs01115513_m1, Leptin gene primer: Hs00174877_m1, AdipoQ gene primer: Hs00605917_m1, FABP4 gene primer: Hs01086177_m1), The result is shown in FIG. 3 and FIG. 4. The isolated human dermis-derived adult stem cells showed about 2 times higher expression of the genes as compared to the dermis-derived fibroblasts. The increase in expression was statistically significant when tested by the paired Student's t-test with p≤0.05.

[Example 6] Selection of Growth Factors Specifically Secreted in Isolated Human Dermis-Derived Adult Stem Cells The expression pattern of growth factors secreted from the culture of the isolated human dermis-derived adult stem cells was investigated using a growth factor array (Raybio, Norcross, Ga., USA).

The isolated human dermis-derived adult stem cells and dermis-derived fibroblasts were seeded onto a 6-well culture dish, with $20 \times 10^4$ cells per well. After culturing the cells, the culture was assayed using the growth factor array. The cell culture was treated with 2 mL of blocking buffer at room temperature for 30 minutes and then 1 mL of the culture was incubated at room temperature for 2 hours. Subsequently, after washing 5 times with 2 mL of washing buffer for 5 minutes, the culture was reached at room temperature for 2 hours with biotinylated anti-growth factor antibody. After further washing 5 times with 2 mL of washing buffer for 5 minutes, the culture was treated with 2 mL of HRP-conjugated streptavidin, incubated for 2 hours, washed with washing buffer, incubated with detection buffer and developed with LAS-3000 (Fuji Film).

Figure 5:
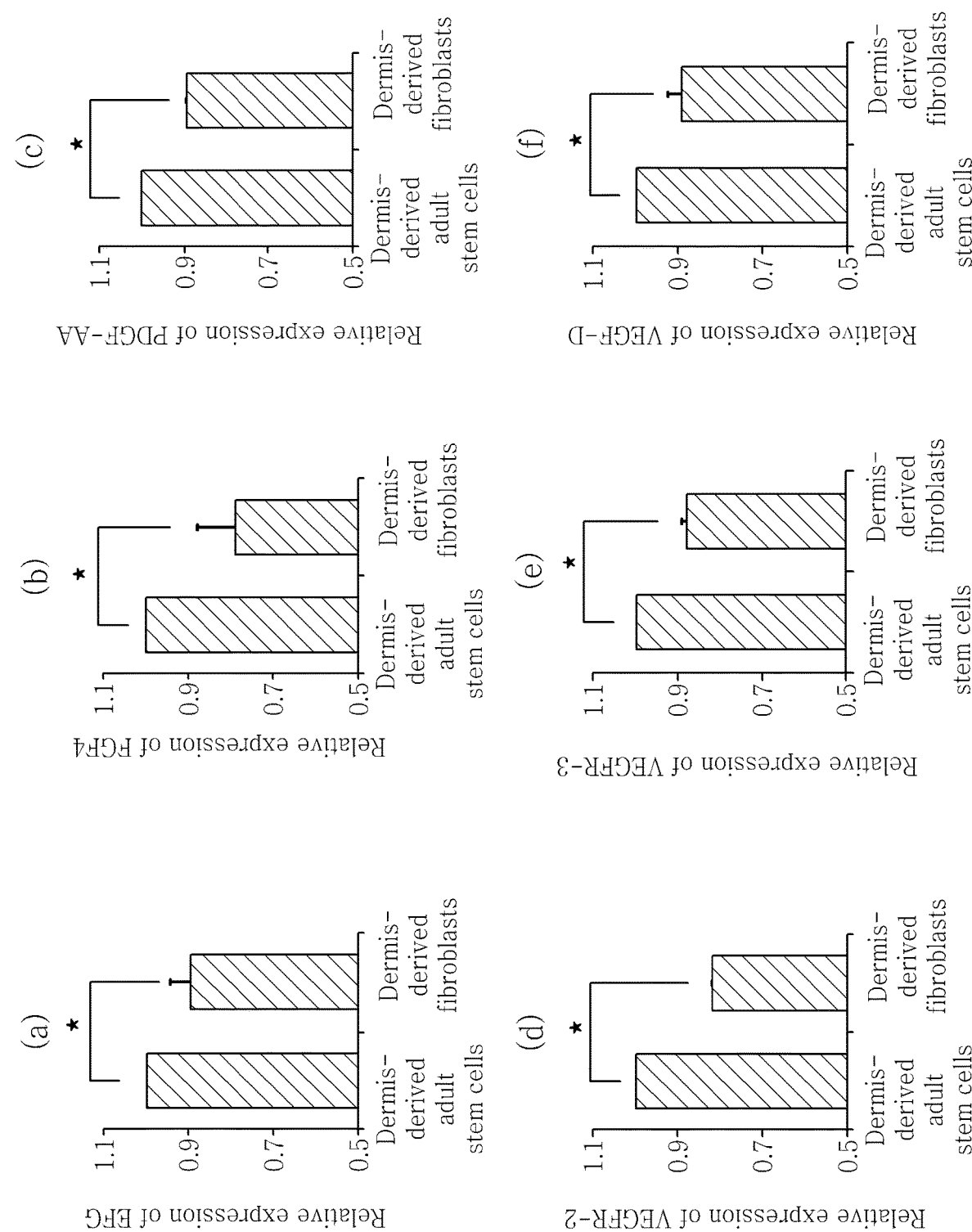
FIG. 5 shows that cell growth factors EGF (a) and FGF4 (b) and angiogenic factors PDGF-A (c), VEGFR-2 (d), VEGFR-3 (e) and VEGF-D (f) are overexpressed in isolated skin dermis-derived adult stem cells as compared to skin dermis-derived fibroblasts.
Figure 6:
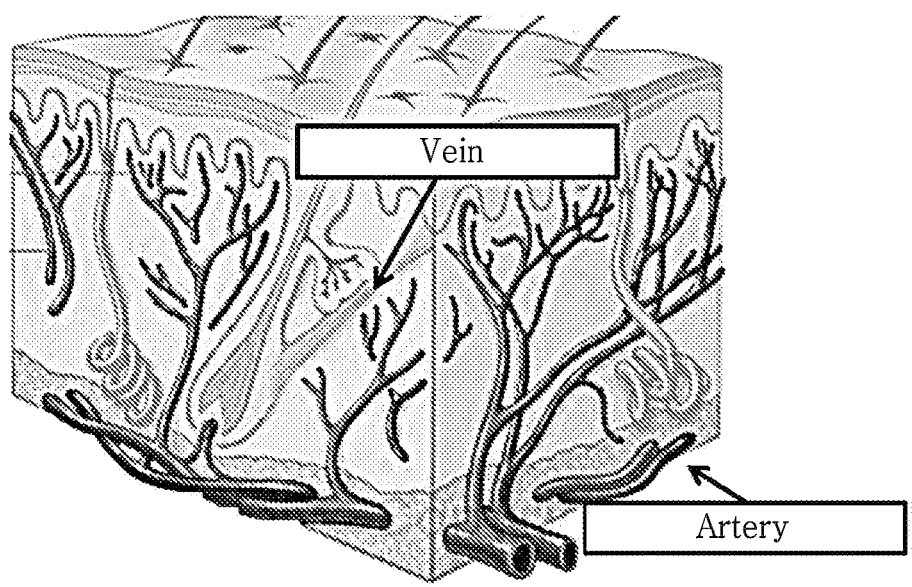
FIG. 6 shows blood vessels present in the skin dermis.
Figure 7:
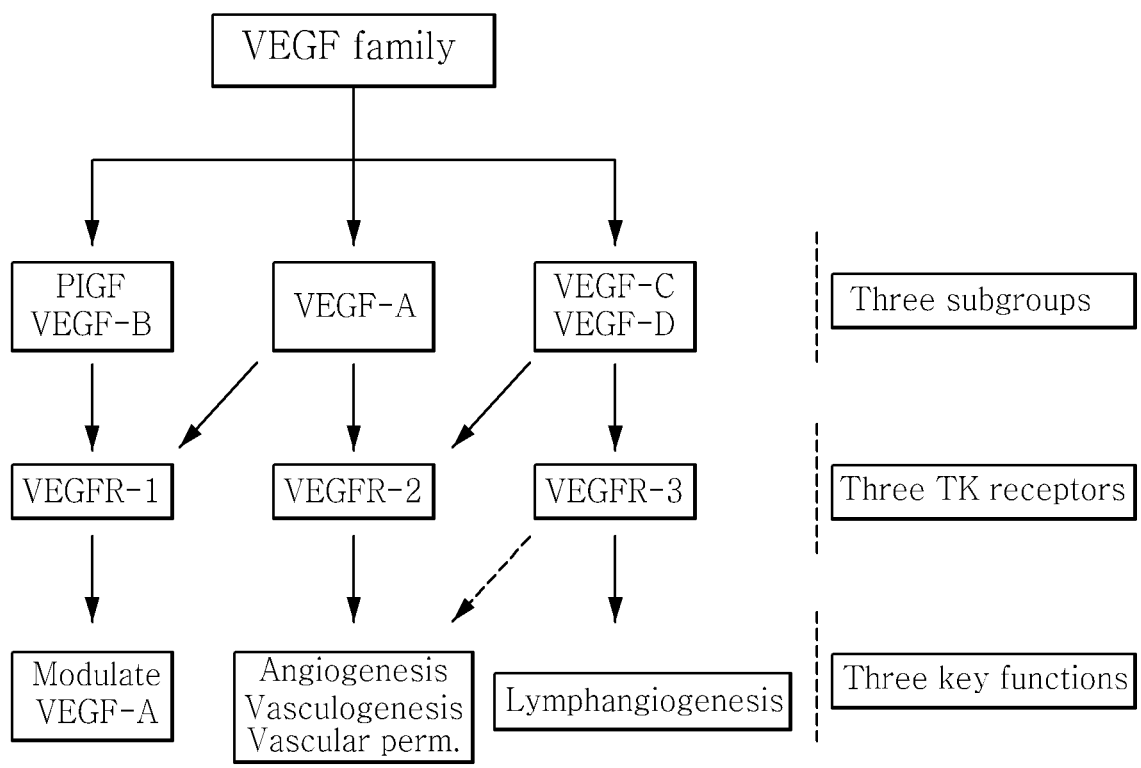
FIG. 7 shows the genealogy of angiogenic factors.

A total of 41 kinds of growth factors were analyzed. When compared with the culture of the human dermis-derived fibroblasts, the culture of the human dermis-derived adult stem cells showed 10% or more increase for the growth factors EGF, FGF4, PDGF-AA, VEGFR-2, VEGFR-3 and VEGF-D (FIG. 5). In particular, since EGF and FGF4 are important growth factors for growth of the epidermis and fibroblasts, the human dermis-derived adult stem cells isolated in the present disclosure are expected to be helpful in treating and recovery of aged or damaged dermis. Also, since VEGFR-2, VEGFR-3 and VEGF-D are important growth factors involved in angiogenesis, the human dermis-derived adult stem cells isolated in the present disclosure may ensure supply of nutrients to the dermis by allowing the growth or migration of capillary vessels (see FIG. 6 and FIG. 7).

The increase in the expression of the growth factors was statistically significant when tested by the paired Student's t-test with p≤0.05.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

[Accession No.]
Depository authority: Korea Research Institute of Bioscience and Biotechnology
Accession No.: KCTC11995BP
Date of deposition: Aug. 8, 2011

INDUSTRIAL APPLICABILITY

A composition containing the human skin dermis-derived adult stem cells of the present disclosure, osteoblasts differentiated from the stem cells or adipocytes differentiated from the stem cells may be used as a composition for osteogenesis or adipogenesis.

The invention claimed is:

1. A method for isolating human skin dermis-derived adult stem cells, comprising
    subculturing human skin dermis-derived fibroblasts;
    reacting the subcultured cells with gelatin or type 4 collagen for 1-5 minutes;
    separating the cells adhering to the gelatin or type 4 collagen;
    confirming vimentin and nestin are expressed in the human skin dermis-derived adult stem cells; and
    confirming S100b (S100 calcium binding protein B) gene is overexpressed in the human skin dermis-derived adult stem cells as compared to the human skin dermis-derived fibroblasts,
    wherein the subculturing of human skin dermis-derived fibroblasts is subculturing fibroblasts derived from dermis of adult skin 2 to 3 times, and
    wherein the stem cells are stem cells of Accession No: KCTC11995BP.

2. The method for isolating human skin dermis-derived adult stem cells according to claim 1, wherein the gelatin is dissolved in distilled water to a concentration of 0.1-1 wt % and the type 4 collagen is dissolved in distilled water to a concentration of 10-30 μg/mL and then reacted with the human skin dermis-derived fibroblasts.

3. The method for isolating human skin dermis-derived adult stem cells according to claim 1, wherein the gelatin or the type 4 collagen is coated on a substrate at 0-10° C. for 16-24 hours and then reacted with the human skin dermis-derived fibroblasts.

4. The method for isolating human skin dermis-derived adult stem cells according to claim 1, which further comprises confirming whether Sox2 (SRY (sex determining region Y)-box 2) gene is overexpressed as compared to the human skin dermis-derived fibroblasts.

5. The method for isolating human skin dermis-derived adult stem cells according to claim 1, which further comprises confirming whether one or more growth factor selected from a group consisting of EGF (epidermal growth factor), FGF4 (fibroblast growth factor 4), PDGF-AA (platelet-derived growth factor-AA), VEGFR-2 (vascular endothelial growth factor receptor 2), VEGFR-3 (vascular endothelial growth factor receptor 3) and VEGF-D (vascular endothelial growth factor D) is overexpressed as compared to the human skin dermis-derived fibroblasts.

* * * * *